US010583465B2

(12) United States Patent
Wang et al.

(10) Patent No.: US 10,583,465 B2
(45) Date of Patent: Mar. 10, 2020

(54) 30 NM IN-LINE LPC TESTING AND CLEANING OF SEMICONDUCTOR PROCESSING EQUIPMENT

(71) Applicant: Applied Materials, Inc., Santa Clara, CA (US)

(72) Inventors: Jianqi Wang, Fremont, CA (US); William Ming-ye Lu, Sunnyvale, CA (US); Yixing Lin, Saratoga, CA (US); Kevin A. Papke, Portland, OR (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 223 days.

(21) Appl. No.: 15/487,213

(22) Filed: Apr. 13, 2017

(65) Prior Publication Data

US 2017/0299487 A1    Oct. 19, 2017

Related U.S. Application Data

(60) Provisional application No. 62/322,523, filed on Apr. 14, 2016.

(51) Int. Cl.
*B08B 3/12* (2006.01)
*G01N 1/38* (2006.01)
*G01N 15/14* (2006.01)
*G01N 1/02* (2006.01)

(52) U.S. Cl.
CPC .............. *B08B 3/12* (2013.01); *G01N 1/38* (2013.01); *G01N 2001/028* (2013.01); *G01N 2001/383* (2013.01); *G01N 2015/1486* (2013.01)

(58) Field of Classification Search
CPC .............. G01N 1/38; G01N 2001/383; G01N 2001/028; G01N 2015/1486; B08B 3/12
See application file for complete search history.

(56) References Cited

U.S. PATENT DOCUMENTS 6,211,956 B1    4/2001  Nicoli
6,491,872 B1 *  12/2002 Wick ................... G01N 1/2273
                                                422/548
6,931,950 B2    8/2005  Malachowski et al.
(Continued)

FOREIGN PATENT DOCUMENTS

JP    H01244633 A    9/1989
JP    H0743289 A     2/1995

OTHER PUBLICATIONS

International Search Report and Written Opinion in related application PCT/US2017/023642, dated Jun. 29, 2017.

*Primary Examiner* — Nimeshkumar D Patel
*Assistant Examiner* — Gedeon M Kidanu
(74) *Attorney, Agent, or Firm* — Patterson + Sheridan LLP

(57) ABSTRACT

The implementations described herein generally relate to 30 nm in-line liquid particle count testing equipment which analyses and cleans semiconductor processing equipment. More specifically, the implementations described relate to a system for diluting, analyzing, and modifying fluids to enable the observation of the contents of the fluids. A dilution sampling tool is coupled with a liquid particle detector for reading the contents of an extraction solution containing particles from semiconductor processing equipment, such as a liner, a shield, a faceplate, or a showerhead, in a cleaning tank. As such, accurate liquid particle readings may be had which reduce oversaturation of the particle detector.

9 Claims, 3 Drawing Sheets

(56) References Cited

U.S. PATENT DOCUMENTS

| | | | |
|---|---|---|---|
| 8,404,056 B1 | 3/2013 | Chen et al. | |
| 2002/0154567 A1* | 10/2002 | Husher | B01F 3/088 366/132 |
| 2003/0174306 A1* | 9/2003 | Grant | G01N 1/38 356/36 |
| 2007/0295063 A1* | 12/2007 | Cho | B24B 57/02 73/61.71 |
| 2012/0216833 A1* | 8/2012 | Wang | H01L 21/67051 134/10 |
| 2014/0146157 A1 | 5/2014 | Duplisea et al. | |
| 2014/0261824 A1* | 9/2014 | Byers | B24B 57/02 137/896 |
| 2015/0330886 A1* | 11/2015 | Ho | B01F 11/0071 356/336 |
| 2016/0056061 A1* | 2/2016 | Wang | H01L 21/67051 134/56 R |

* cited by examiner ered to the semiconductor processing world.

30 NM IN-LINE LPC TESTING AND CLEANING OF SEMICONDUCTOR PROCESSING EQUIPMENT

CROSS-REFERENCE TO RELATED APPLICATIONS

This application claims benefit of U.S. provisional patent application Ser. No. 62/322,523, filed Apr. 14, 2016, which is herein incorporated by reference.

BACKGROUND

Field

Implementations of the present disclosure generally relate to testing and cleaning of semiconductor processing equipment, and more specifically to an apparatus and method for diluting, analyzing, and modifying fluids to enhance the observation of the contents of the fluids.

Description of the Related Art

An optical/flow system may be employed for transporting a fluid within an analytical instrument to an imaging and optical analysis area. A liquid sample is typically delivered into the bore of a chamber and the sample is interrogated in some way to generate analytical information concerning the nature or properties of the sample. The sample may be stagnant or flowing. In some arrangements, a light source may be directed to the chamber to illuminate the contents therein. Obtaining scattered light has been and remains a reasonable way to detect and observe contents of samples, particularly fluid samples. It is desirable in doing the interrogation to avoid having too many particles in the viewing field so that the contents may be discerned in an effective manner. Fluids of interest may vary widely in their viscosities and particle or solids density. Fluids with low levels of solids are more easily observed for content information than are fluids including high levels of solids. Nevertheless, there are fluids loaded with high solids contents for which analysis may be desired.

It is possible to examine the contents of heavily loaded fluids through various observational and analytical tools. Unfortunately, these analytical tools or these heavily loaded fluids may necessitate considerable time to condition the fluid sufficiently to receive a reasonable portrayal of the contents, and the evaluation process itself can be time consuming and relatively costly.

In the semiconductor processing art additional challenges remain in measuring liquid particles from an extraction solution from a semiconductor chamber component inside a cleaning tank. Often the extraction solution, once combined with particles removed from the semiconductor chamber component, contains a large amount of particles greater than or equal to 30 nm, which may saturate the liquid particle count detector if sampled directly from the extraction solution, thus leading to inaccurate readings.

Therefore, what is needed is a system and method to enable efficient and accurate analysis of the contents of a fluid with high 30+ nm solids content. What is also needed in the art is an apparatus and method for diluting a sample in a cleaning tank such that 30+ nm liquid particles may be detected and counted efficiently and accurately without saturating the detector.

SUMMARY

The implementations described herein generally relate to 30 nm in-line liquid particle count testing equipment which analyses and cleans semiconductor processing equipment. More specifically, the implementations described relate to a system for diluting, analyzing, and modifying solutions to enable the observation of the contents of the solutions. A dilution sampling tool is coupled with a liquid particle detector for reading the contents of an extraction solution containing particles from semiconductor processing equipment, such as a liner, a shield, a faceplate, a showerhead, or the like, in a cleaning tank. As such, accurate liquid particle readings may be obtained, due to the reduction of the oversaturation the particle detector.

In one embodiment, a liquid particle counting system is disclosed. The liquid particle counting system includes a holding tank, a first pump operatively connected to the holding tank, and a dilution system operatively connected to the first pump. The liquid particle counting system also includes a dilution source operatively connected to the dilution system, a liquid particle counter operatively connected downstream to the dilution system, and at least one flow meter operatively connected to the liquid particle counter.

In another embodiment, a liquid particle counting system is disclosed. The liquid particle counting system includes a holding tank. The holding tank includes a holding area and a sonicator separated from the holding area by a first wall. The liquid particle counting system further includes a first pump coupled downstream to the holding area by a first tube, a dilution system coupled downstream to the first pump by a second tube, a dilution source coupled downstream to the dilution system by a third tube, and a liquid particle counter coupled downstream to the dilution system by a fourth tube.

In yet another embodiment, a method for counting liquid particles of a semiconductor component is disclosed. The method includes immersing the semiconductor component inside a holding tank, wherein the holding tank comprises an extraction solution, and passing various levels of ultrasonication energy to the holding tank to form a particle solution, wherein the particle solution comprises the extraction solution and a plurality of particles from the semiconductor component. The method further includes pumping the particle solution to a dilution system, diluting the particle solution with de-ionized water to form a diluted solution, and transferring the diluted solution to a liquid particle counter, wherein the liquid particle counter determines the numbers of liquid particles in the diluted solution in real-time. The method also includes transferring the diluted solution through a flow meter, and combining the diluted solution with the extraction solution in the holding tank.

BRIEF DESCRIPTION OF THE DRAWINGS

So that the manner in which the above recited features of the present disclosure can be understood in detail, a more particular description of the disclosure, briefly summarized above, may be had by reference to implementations, some of which are illustrated in the appended drawings. It is to be noted, however, that the appended drawings illustrate only exemplary implementations and are therefore not to be considered limiting of its scope, may admit to other equally effective implementations.

Figure 1:
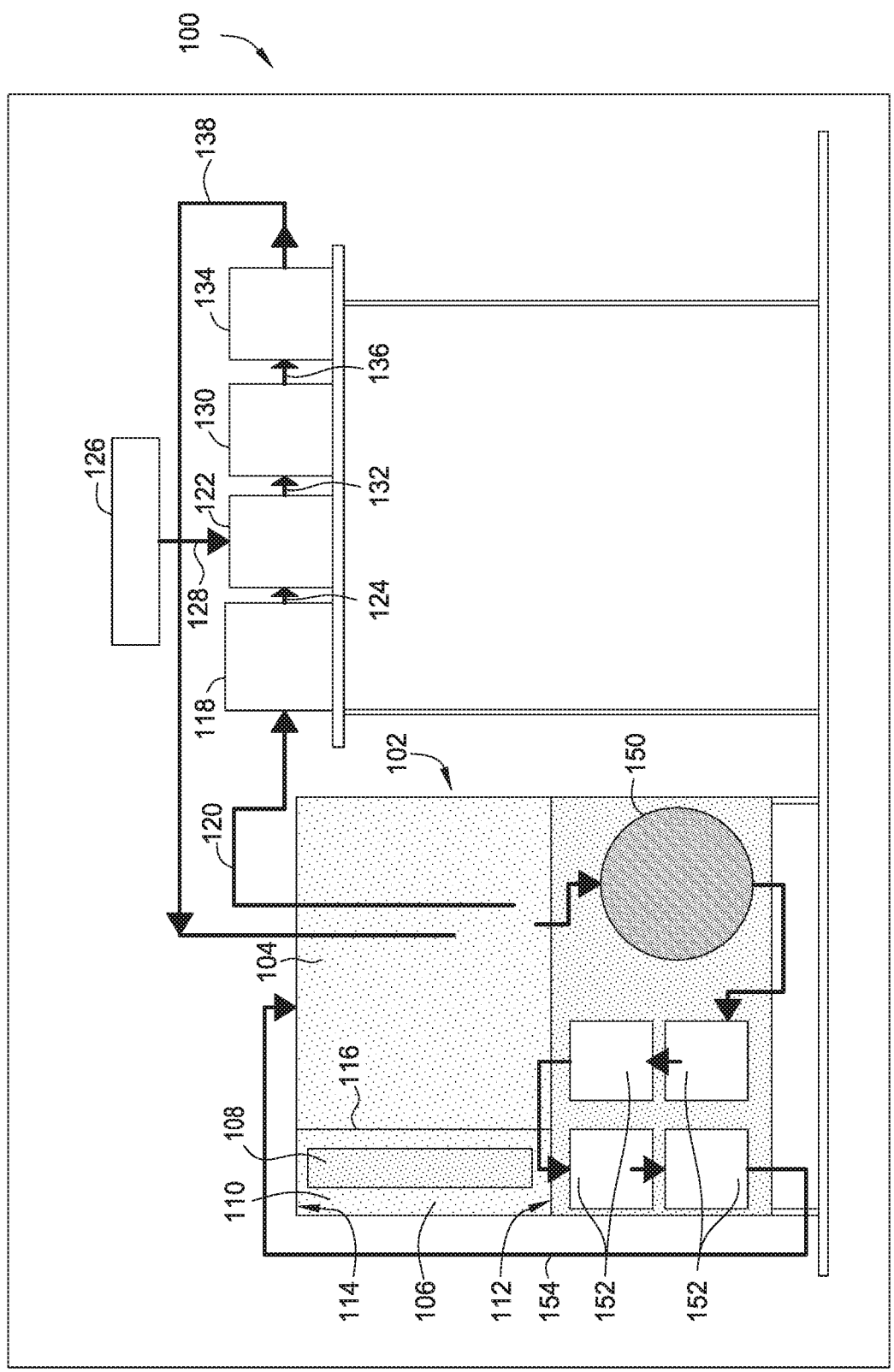
FIG. 1 illustrates a schematic side view of a liquid particle counting system, according to implementations described herein.

To facilitate understanding, identical reference numerals have been used, where possible, to designate identical elements that are common to the figures. It is contemplated that elements and features of one embodiment may be beneficially incorporated in other implementations without further recitation.

DETAILED DESCRIPTION

The implementations described herein generally relate to 30 nm in-line liquid particle count testing equipment which analyses and cleans semiconductor processing equipment. More specifically, the implementations described relate to a system for diluting, analyzing, and modifying solutions to enable the observation of the contents of the solutions. A dilution sampling tool is coupled with a liquid particle detector for reading the contents of an extraction solution containing particles from semiconductor processing equipment, such as a liner, a shield, a faceplate, a showerhead, or the like, in a cleaning tank. As such, accurate liquid particle readings may be had which reduce oversaturation the particle detector.

FIG. 1 schematically illustrates a liquid particle counting system 100, according to one implementation. The liquid particle counting system 100 allows for the dilution, analysis, and modification of a solution such that observations of the solution may be had. The liquid particle counting system 100 includes a holding tank 102. The holding tank 102 may comprise a polypropylene material, a quartz material, a polyethylene material, a polytetrafluoroethylene material, other suitable materials, or mixtures and combinations thereof. Furthermore, in certain implementations, the holding tank 102 may be elevated or raised such as by a lift table (not shown). The holding tank 102 may be configured to hold a liquid solution therein, such as, by way of example only, deionized water.

In some implementations, the holding tank 102 may include a first holding area 104 and a second holding area 106. The first holding area 104 may be configured to hold the liquid solution therein, as described supra. The second holding area 106 may be disposed adjacent the first holding area 104, and disposed within the same holding tank 102. In some implementations, the second holding area 106 may also be configured to hold a liquid solution material. The first holding area 104 and the second holding area 106 may be separated by a first wall 116. The first wall 116 may comprise a polypropylene material, a quartz material, a polyethylene material, a polytetrafluoroethylene material, other suitable materials, or mixtures and combinations thereof. The first wall 116 may allow energy or waves to propagate therethrough. The first wall 116 may extend the length of the holding tank 102 or a portion thereof.

In some embodiments, semiconductor processing equipment or a part thereof, such as a liner, a shield, a faceplate, a showerhead, or the like, may be disposed within the first holding area 104. Furthermore, in some embodiments, used semiconductor processing equipment may be disposed within the first holding area 104 for cleaning and/or analysis. The first holding area 104 may further comprise an extraction solution, such as deionized water. The semiconductor processing equipment disposed within the first holding area 104 comprising the extraction solution, such that the semiconductor processing equipment is immersed within the extraction solution.

The second holding area 106 may comprise a sonicator 108 disposed therein. In some implementations, the sonicator 108 may be coupled to a sidewall 110, a floor 112, and/or a lid 114 of the second holding area 106. In other implementations, the sonicator 108 may be disposed in a liquid solution within the second holding area 106, such as, the extraction solution, for example, deionized water. Also, in some embodiments, the sonicator 108 may contact the holding tank 102. In some implementations, the sonicator 108 may be operatively connected to a power source. When operating, the sonicator 108 may agitate, vibrate, shake, and/or sonicate within the liquid solution, to disturb the area surrounding the sonicator 108 and pass energy or waves through the first wall 116 between the second holding area 106 and the first holding area 104. In some embodiments, the sonicator 108 may not be submerged within a liquid solution, but rather may be coupled to first wall 116 and/or a sidewall 110 of the second holding area 106 in order to provide agitation. By providing agitation, the sonicator 108 may allow particles from the semiconductor component disposed within the first holding area 104 to be disturbed, thus allowing particles from the semiconductor component to be introduced into the extraction solution, so as to create a particle solution. As such, the particle solution may include, for example, deionized water and particles from the semiconductor component. The particle solution may be utilized for accurately counting particles contained therein.

In some embodiments, the sonicator 108 may be attached to a lead screw and motor (not shown) to move the sonicator 108 back and forth across the length of the second holding area 106. In some embodiments, the sonicator 108 may be raised and lowered as the sonicator 108 is moved back and forth across the length of the second holding area 106. In some embodiments, a plurality of sonicators 108 may be disposed within the second holding area 106 and may be controlled in operation by turning the sonicators 108 on and off to simulate the movement of a sonicator within the second holding area 106. It has been found that by moving the sonicator 108, or simulating the movement of sonicator 108, during the agitation operation creating energy or waves to disturb particles on the semiconductor components, can prevent the undesirable energy concentration or wave reflected from a fixed location on the semiconductor components and therefore results in reduced micro-pitting of the semiconductor components caused by the agitation operation. In addition, it was found that by moving the sonicator 108, or simulating the movement of sonicator 108, it is not necessary to stop the agitation operation, open the tank and reach in with a gloved hand to turn and rotate the part, and subsequently resume the agitation process, as is the typical operation process. Because the agitation operation is not interrupted with the movement of the sonicator 108, the process time is reduced and the opportunity to contaminate the particle solution by reaching into the tank is also greatly reduced.

The liquid particle counting system 100 further includes a first pump 118. The first pump 118 may be disposed downstream from the holding tank 102. The first pump 118 is operatively connected to the holding tank 102, and in some implementations, the first pump 118 may be operatively connected to the first holding area 104 by a first tube 120. The first pump 118 may be a peristaltic pump. The first pump 118 may pump the particle solution from the first holding area 104 through the dilution system 122, discussed infra.

As utilized herein, a "tube" may include any tubular or hollow apparatus for transferring liquid and/or materials from a first location to a second location. By way of example only, a tubular may include a pipe, a tube, a straw, or the like, and may include any suitable material. Furthermore, the tubular may be rigid or flexible.

In some implementations, the first tube 120 comprises a vinyl material, a polymeric material, a perfluoroalkoxy material, a nylon material, or combinations and mixtures thereof. The first tube 120 may comprise a clear material, an opaque material, a translucent material, or a transparent material. In some implementations, liquid may be viewable through the first tube 120. Furthermore, in some implementations, the first tube 120 may be weldable.

The liquid particle counting system 100 also includes a dilution system 122. The dilution system 122 may be disposed downstream of the first pump 118. The dilution system 122 is operatively connected to the first pump 118, and in some implementations, the dilution system 122 is coupled to the first pump 118. The dilution system 122 may control the dilution ratio. The dilution system 122 may be coupled to the first pump 118 by a second tube 124. The second tube 124 comprises a vinyl material, a polymeric material, a perfluoroalkoxy material, a nylon material, or combinations and mixtures thereof. The second tube 124 may comprise a clear material, an opaque material, a translucent material, or a transparent material. In some implementations, liquid may be viewable through the second tube 124. Furthermore, in some implementations, the second tube 124 may be weldable.

In some implementations, the dilution system 122 may be a LiquiTrak® Precision Dilution System, model 6138 commercially available from FMT.

The liquid particle counting system 100 further includes a dilution source 126. The dilution source 126 is operatively connected to the dilution system 122. In some implementations, the dilution source 126 directly feeds additional dilution solution into the dilution system 122. The dilution source 126 may be coupled to the dilution system 122 by a third tube 128. The third tube 128 comprises a vinyl material, a polymeric material, a perfluoroalkoxy material, a nylon material, or combinations and mixtures thereof. The third tube 128 may comprise a clear material, an opaque material, a translucent material, or a transparent material. In some implementations, liquid may be viewable through the third tube 128. Furthermore, in some implementations, the third tube 128 may be weldable.

In some implementations, the dilution source 126 adds additional dilution solution to the extraction solution provided to the dilution system 122 from the first pump 118. In some embodiments, the dilution solution may comprise additional deionized water. As such, the dilution source 126 may provide deionized water to the dilution system 122 to create a diluted particle solution. By combining additional dilution solution to the particle solution to form a diluted particle solution, saturation of a sensor in the liquid particle counter 130, discussed infra, may be prevented. Between exiting the dilution source 126 and before entering the dilution system 122, the additional dilution solution from the dilution source 126 may pass through at least one filter.

A dilution factor D may be utilized to determine the amount of dilution solution to add to the dilution system 122. The dilution factor D is defined below in Equation 1. $F_d$ represents the liquid flow rate through the diluent path (mL/min), $F_r$ represents the liquid flow rate through the liquid particle counter (LPC) 130 (mL/min), discussed infra, and $F_s$ represents the sample liquid flow rate from the LPC tank (mL/min).

$$D=(F_d+F_r)/F_s \quad \text{(Equation 1)}$$

The liquid particle counting system 100 may further include a liquid particle counter 130. The liquid particle counter 130 is operatively connected to the dilution system 122, and in some implementations, the liquid particle counter 130 is coupled to the dilution system 122 by a fourth tube 132. The liquid particle counter 130 may be disposed downstream of the dilution system 122.

The fourth tube 132 comprises a vinyl material, a polymeric material, a perfluoroalkoxy material, a nylon material, or combinations and mixtures thereof. The fourth tube 132 may comprise a clear material, an opaque material, a translucent material, or a transparent material. In some implementations, liquid may be viewable through the fourth tube 132. Furthermore, in some implementations, the fourth tube 132 may be weldable.

In some implementations, the liquid particle counter 130 may be an LPC detector such as the NanoCount 30+ Liquid Particle Counter commercially available from Lighthouse Worldwide Solutions, Fremont, Calif.

The liquid particle counting system 100 further includes at least one flow meter 134. The at least one flow meter 134 is operatively connected to the liquid particle counter 130, and in some implementations, the at least one flow meter 134 is coupled to the liquid particle counter 130 by a fifth tube 136. The at least one flow meter 134 may be disposed downstream of the liquid particle counter 130. In some implementations, it is contemplated that the at least one flow meter 134 may be built in and/or integrated within the liquid particle counter 130.

The fifth tube 136 comprises a vinyl material, a polymeric material, a perfluoroalkoxy material, a nylon material, or combinations and mixtures thereof. The fifth tube 136 may comprise a clear material, an opaque material, a translucent material, or a transparent material. In some implementations, liquid may be viewable through the fifth tube 136. Furthermore, in some implementations, the fifth tube 136 may be weldable.

The at least one flow meter 134 may further be operatively connected to the first holding area 104 by a sixth tube 138. The sixth tube 138 may return the diluted extraction solution exiting the flow meter to the first holding area 104. As such, the diluted particle solution may be recycled.

In some implementations, the first pump 118, the dilution system 122, the liquid particle counter 130, and/or the at least one flow meter 134 may be elevated, such as disposed on a raised platform.

It is contemplated that, in some embodiments, the diluted particle solution may not be returned to the first holding area 104. As such, in some embodiments, the diluted particle solution may be distributed to a waste disposal area after exiting the at least one flow meter 134.

Furthermore, in some implementations, the liquid particle counting system 100 may further include a second pump 150. The second pump 150 may be disposed below the holding tank 102, such that the second pump 150 is gravity fed. The second pump 150 may pump solution (which may include diluted particle solution, extraction solution, and filtered solution, discussed infra) from the first holding area 104 through at least one particle filter 152. In some implementations, the solution may be pumped through a plurality of particle filters 152. The plurality of particle filters 152 may be arranged in series or in parallel and each particle filter 152 may filter particles out of the solution passing therethrough. In some embodiments, the plurality of particle filters 152 may include particle filters which filter various sizes of particles. The plurality of particle filters 152 may be coupled to the first holding area 104 of the holding tank 102 downstream of the plurality of particle filters 152, such that the filtered solution may be recombined and deposited in the first holding area 104. In some implementations, a seventh tube 154 may couple an exit of the plurality of particle filters 152 to the first holding area 104.

Figure 2:
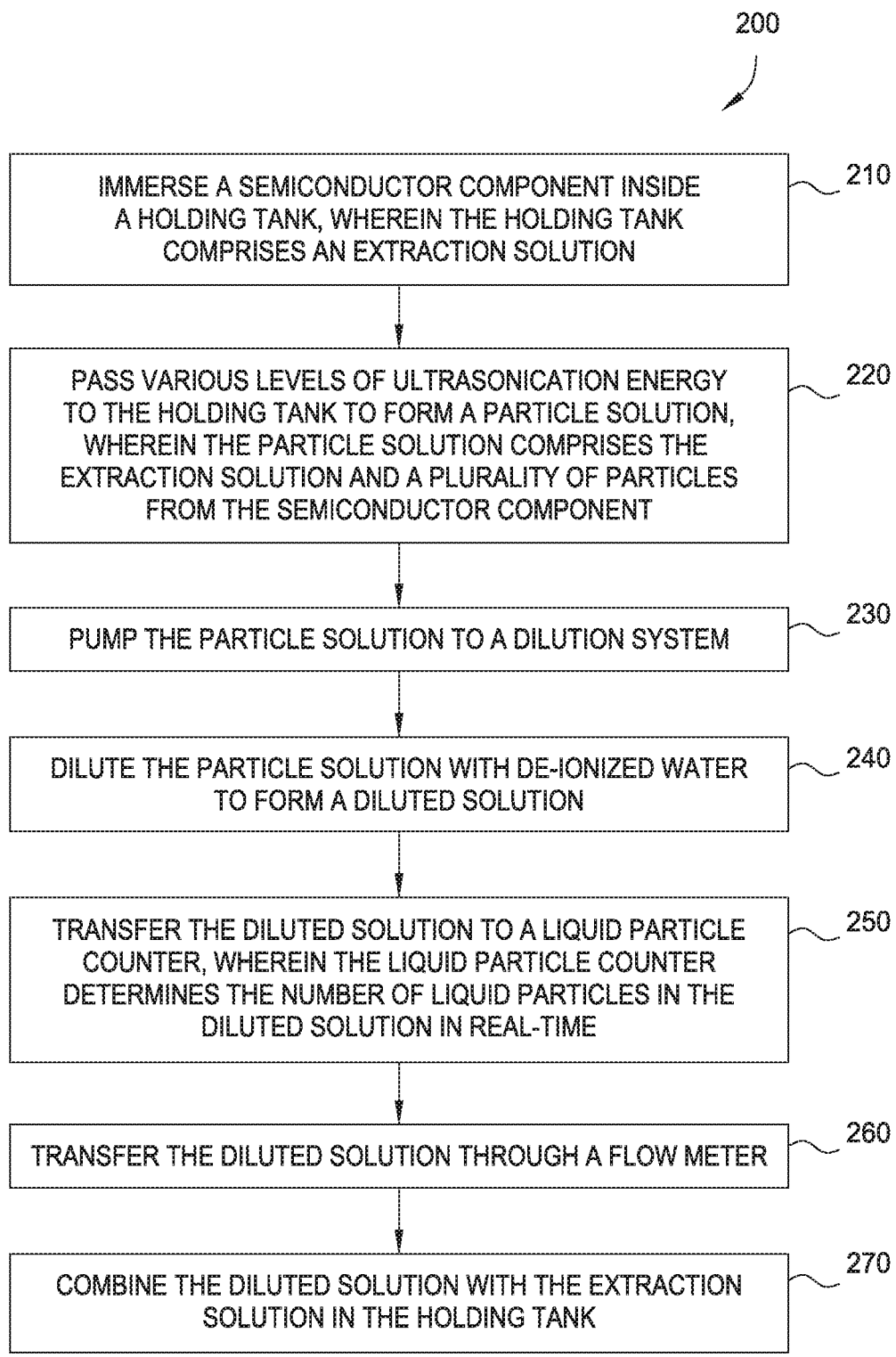
FIG. 2 illustrates a schematic illustrates operations of a method for counting liquid particles of a semiconductor component, according to implementations described herein.

FIG. 2 schematically illustrates operations of a method 200 for counting liquid particles of a semiconductor component, according to one embodiment. Numerous different semiconductor components may be tested and/or cleaned utilizing the method 200 disclosed, including, for example, liners, shields, faceplates, showerheads, and the like.

At operation 210, the semiconductor component is immersed inside a holding tank, such as holding tank 102, discussed supra. The semiconductor component may be immersed within an extraction solution disposed within the holding tank, such as a deionized water extraction solution.

At operation 220, various levels of energy are passed through the area of the holding tank in which the semiconductor component is disposed. In some embodiments, various levels of ultrasonicated energy may be passed to the holding tank to form a particle solution. The energy may agitate and/or vibrate the semiconductor component and/or the extraction solution to remove or loosen particles from the semiconductor component. The loosened or removed particles may combine with the extraction solution to form the particle solution. As such, the particle solution may comprise a combination of the extraction solution and a plurality of particles from the semiconductor component.

At operation 230, the particle solution is pumped from the holding tank to a dilution system. The particle solution may be pumped by a peristaltic pump via the first tube, discussed infra.

At operation 240, the particle solution is diluted with deionized water to form a diluted particle solution. In order to form the diluted particle solution, additional extraction solution, deionized water, or other dilution solutions may be added to particle solution within the dilution system.

At operation 250, the diluted particle solution is transferred to a liquid particle counter. The liquid particle counter may analyze the diluted solution and determine the number of liquid particles from the semiconductor component contained within the diluted solution. In some embodiments, the liquid particle counter may determine the number of liquid particles therein in real time.

At operation 260, the diluted particle solution is transferred to and through a flow meter. The flow meter may measure the rate of flow of the diluted particle solution through the system, and/or control the flow of the diluted particle solution therethrough. Furthermore, at operation 270, the diluted particle solution is combined with the extraction solution held in the holding tank. As such, the diluted particle solution is recycled by being re-added to the holding tank.

Figure 3:
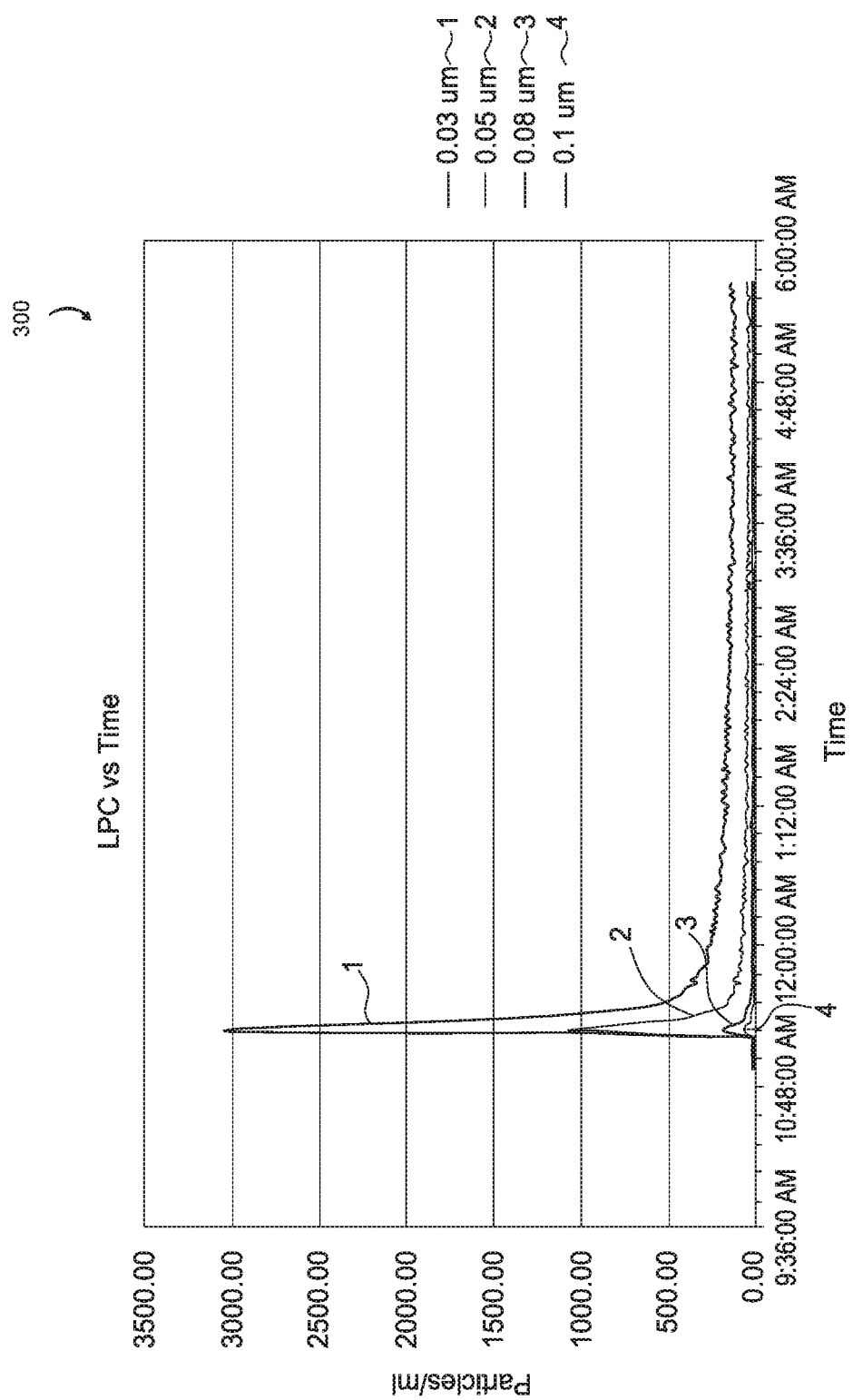
FIG. 3 illustrates a data plot of liquid particles counted versus time for a liquid particle counter baseline run of de-ionized water in a holding tank with a 0.1 micrometer filter filtration system applied thereto, according to implementations described herein.

FIG. 3 illustrates a data plot 300 of LPC versus time for a liquid particle counter baseline run of de-ionized water in a holding tank with a 0.1 micrometer filter filtration system. As shown, unexpected results were achieved in that a stable baseline of liquid particles counted was achieved.

Testing was performed and results indicate that an in-line 30 nm LPC detector was successfully set up with a LPC analysis tank through a precision dilution system as the dilution sampler. A stable de-ionized water baseline was achieved both with and without sonication. Furthermore, the de-ionized water source used for dilution had a baseline particles of 17 p/mL at the >30 nm size. Also, it was determined that the peristaltic pump generated particles at the higher pump rate, and as such, the optimal flow rate was determined to be between about 0.11 ml/min and about 0.27 ml/min, for example, between about 0.18 ml/min and about 0.23 ml/min. Additionally, the working range of the dilution system was determined to be between about 400× and about 6000×. A linear relationship between LPC readings and the 1/D (dilution ratio) was obtained, and results indicated that the linear relationship was consistent with the mathematical calculation. Furthermore, two cleanroom components were each testing using the system disclosed herein and each proved to be successful in that detector saturation was reduced.

Benefits of the present disclosure include an in-line dilution system which may be utilized as a dilution sampling tool to link a 30 nm LPC detector to an extraction solution in a cleaning tank. This system relieved the detector saturation problem when the particle amount is too high to be measured directly from the extraction solution, and allows for actual LPC readings to be obtained.

In summation, the extraction solution from a semiconductor component typically contains a large amount of 30+ nm particles, which may saturate the liquid particle counter (LPC) detector if sampled directly, thus leading to wrong readings. As such, a dilution system for diluting the extraction solution and a liquid particle counter as an in-line detector to measure liquid particles from an extraction solution from a semiconductor chamber component inside a cleaning tank is disclosed. The implementations described herein generally relate to 30 nm in-line liquid particle count testing equipment which analyses and cleans semiconductor processing equipment. More specifically, the implementations described relate to a system for diluting, analyzing, and modifying fluids to enable the observation of the contents of the fluids. A dilution sampling tool is coupled with a liquid particle detector for reading the contents of an extraction solution containing particles from semiconductor processing equipment, such as a liner, a shield, a faceplate, a showerhead, in a cleaning tank. As such, accurate liquid particle readings may be obtained which reduces oversaturation of the particle detector.

While the foregoing is directed to implementations of the present disclosure, other and further implementations of the disclosure may be devised without departing from the basic scope thereof, and the scope thereof is determined by the claims that follow.

What is claimed is:

1. A liquid particle counting system, comprising:
   a holding tank, comprising:
      a first holding area;
      a second holding area; and
      a sonicator disposed in the second holding area, wherein the second holding area is separated from the first holding area by a first wall;
   a first pump coupled downstream to the first holding area by a first tube;
   a dilution system coupled downstream to the first pump by a second tube;
   a dilution source coupled to the dilution system by a third tube;
   a liquid particle counter coupled downstream to the dilution system by a fourth tube;

a flow meter operatively connected downstream to the liquid particle counter by a fifth tube; and a sixth tube that connects an outlet of the flow meter to an inlet of the holding tank.

2. The liquid particle counting system of claim 1, wherein the first wall comprises a polypropylene material, a quartz material, a polyethylene material, or combinations thereof.

3. The liquid particle counting system of claim 1, wherein the holding tank comprises a polypropylene material, a quartz material, a polyethylene material, a polytetrafluoroethylene material, or combinations thereof.

4. The liquid particle counting system of claim 1, wherein the first pump is a peristaltic pump.

5. The liquid particle counting system of claim 1, wherein the first tube, the second tube, the third tube, and the fourth tube comprise a vinyl material, a polymeric material, a perfluoroalkoxy material, a nylon material, or combinations and mixtures thereof.

6. The liquid particle counting system of claim 1, further comprising:

a second pump operatively coupled to the first holding area; and at least one particle filter operatively coupled at a first end to the second pump by a seventh tube, wherein the at least one particle filter is operatively coupled at a second end to an inlet of an eighth tube, and wherein the eighth tube has an outlet disposed at an inlet of the holding tank.

7. The liquid particle counting system of claim 6, wherein the second pump is a gravity fed pump.

8. The liquid particle counting system of claim 6, wherein the at least one particle filter is a plurality of particle filters connected in series or in parallel.

9. A method for counting liquid particles of a semiconductor component, comprising:

immersing the semiconductor component inside a holding tank, wherein the holding tank comprises an extraction solution;

passing various levels of ultrasonication energy to the holding tank to form a particle solution, wherein the particle solution comprises the extraction solution and a plurality of particles from the semiconductor component;

pumping the particle solution to a dilution system;

diluting the particle solution with de-ionized water to form a diluted solution;

transferring the diluted solution to a liquid particle counter, wherein the liquid particle counter determines the numbers of liquid particles in the diluted solution in real-time;

transferring the diluted solution through a flow meter; and combining the diluted solution flowing from the flow meter with the extraction solution in the holding tank.

* * * * *